United States Patent [19]
Yoshida et al.

[11] Patent Number: 5,561,221
[45] Date of Patent: Oct. 1, 1996

[54] METHODS AND COMPOSITIONS FOR PROMOTING PROTEIN FOLDING

[75] Inventors: Masasuke Yoshida; Hideki Taguchi; Jin Konishi, all of Yokohama, Japan

[73] Assignee: Nippon Oil Company Limited, Minato-ku, Japan

[21] Appl. No.: 285,346

[22] Filed: Aug. 3, 1994

[30] Foreign Application Priority Data

Aug. 3, 1993 [JP] Japan .................................. 5-210904

[51] Int. Cl.$^6$ ............................ C07K 14/00; C07K 7/00; C07K 1/02; C07K 1/04
[52] U.S. Cl. ........................ 530/350; 530/300; 530/402; 530/409; 435/68.1; 435/69.1; 435/70.1; 435/71.1
[58] Field of Search .................................. 530/350, 409, 530/402, 351, 397, 344, 300, 333, 358, 371, 829; 435/68.1, 70.1, 71.1, 193, 820, 69.1, 69.3, 69.4, 69.52, 69.6

[56] References Cited

U.S. PATENT DOCUMENTS 5,302,518  4/1994  Neupert et al. ...................... 435/69.1

FOREIGN PATENT DOCUMENTS

0412465A1  2/1991  European Pat. Off. .
WO94/23042  10/1994  WIPO .

OTHER PUBLICATIONS

Buchner et al. (1992) "Renaturation of a Single–Chain Immunotoxin Facilitated by Chaperones and Protein Disulfide Isomerase," *Biotechnology* 10:682–685.
Phadtare et al. (1994) "Refolding and Release of Tubulins by a Functional Immobolized GroEL Column," *Biochimica et Biophysica Acta* 1208:189–192.
Alconada et al., (1993) "A Chaperonin Protein Module Involved in Recognition of Interactive Protein Surfaces," *Trends in Biochemical Sciences* 18:81–82.
Azem et al., (1994) "Characterization of a Functional GroEL$_{14}$ (GroES$_7$)$_2$ Chaperonin Hetero–Oligomer," *Science* 265:653–657.
Braig et al., (1993) "A Polypeptide Bound by the Chaperonin GroEL is Localized Within a Central Cavity," *Proc. Natl. Acad. Sci. USA* 90:3978–3982.
Buchner et al., (1991) "GroE Facilities Refolding of Citrate Synthase by Suppressing Aggregation," *Biochemistry* 30:1586–1591.
Chandrasekhar et al. (1986) "Purification and Properties of the GroES Morphogenetic Protein of Escherichia Coli," *Journal of Biological Chemistry* 261: 12414–12419.
Ellis, John (1987) "Proteins as Molecular Chaperones," *Nature* 328:378–379.
Ellis et al., (1991) "Molecular Chaperones," *Annu. Rev. Biochem.* 60:321–347.
Gething et al., (1992) "Protein Folding in the Cell," *Nature* 355:33–45.
Goloubinoff et al., (1989) "Reconstruction of Active Dimeric Ribulose Bisphosphate Carboxylase from an Unfolded State Depends on Two Chaperonin Proteins and Mg–ATP," *Nature* 342:884–889.

(List continued on next page.)

*Primary Examiner*—Mindy Fleisher
*Assistant Examiner*—Nancy J. Degen
*Attorney, Agent, or Firm*—Testa, Hurwitz & Thibeault

[57] ABSTRACT

Disclosed are 1) compositions comprising isolated monomeric subunits of chaperonin-60 or truncated fragments thereof that promote the folding of a polypeptide chain in vitro, 2) monomeric subunits of chaperonin-60 or truncated fragments thereof, immobilized on a solid surface, that promote also the folding of a polypeptide chain in vitro, 3) methods for preparing and/or immobilizing the monomeric subunits of chaperonin-60 or truncated fragments thereof, and 4) methods for folding polypeptide chains, specifically polypeptide chains expressed in a heterologous expression system, in vitro using the monomeric subunits of chaperonin-60 or truncated fragments thereof.

18 Claims, 1 Drawing Sheet

OTHER PUBLICATIONS

Hartl et al., (1992) "Protein Folding in the Cell: The Role of Molecular Chaperones Hsp70 and Hsp60," *Annu. Rev. Biophys. Biomol. Struct.* 21: 293–322.

Hemmingsen et al., (1988) "Homologous Plant and Bacterial Proteins Chaperone Oligometric Protein Assembly," *Nature* 333:330–334.

Hendrix, Roger W. (1979) "Purification and Properties of GroE, a Host Protein Involved in Bacteriophage Assembly," *J. Mol. Biol.* 129:375–392.

Hohn et al., (1979) "Isolation and Characterization of the Host Protein GroE Involved in Bacteriophage Lambda Assembly," *J. Mol. Biol.* 129:359–373.

Horovitz et al., (1993) "Mutation Ala2→Ser Destabilizes Intersubunit Interactions in the Molecular Chaperone GroEL," *J. Mol. Biol.* 231:58–64.

Horovitz et al., (1993) "The N Terminus of the Molecular Chaperonin GroEL is a Crucial Structure Element for Its Assembly," *J. Biol. Chem.* 268:9957–9959.

Ishii et al., (1992) "Structure of Holo–chaperonin Studies with Electron Microscopy," *FEBS Letters* 299:169–174.

Jakob et al., (1993) "Small Heat Shock Proteins Are Molecular Chaperones," *J. Biol. Chem.* 268:1517–1520.

Langer et al., (1992) "Chaperonin–mediated Protein Folding: GroES binds to One End of the GroEL Cylinder, Which Accommodates the Protein Substrate Within its Central Cavity," *J. EMBO* 11:4757–4765.

Lissin et al., (1990) "(Mg–ATP)–dependent self–assembly of Molecular Chaperone GroEL," *Nature* 348:339–342.

Lissin et al., (1993) "Stabilization of a Compact Conformation of Monomeric GroEL at Low Temperature by Adenine Nucleotides," *FEBS Letters* 324:41–44.

Lorimer, George H. (1992) "Role of Accessory Proteins in Protein Folding," *Current Opinion in Structural Biology* 2:26–34.

Martin et al., (1991) "Chaperonin–mediated Protein Folding at the Surface of GroEL Through a 'Molten Globule'–like Intermediate," *Nature* 352:36–42.

Mendoza et al., (1991) "Chaperonins Facilitate the in Vitro Folding of Monomeric Mitochondrial Rhodanese," *J. Biol. Chem.* 266:13044–13049.

Mendoza et al., (1991) "Unassisted Refolding of Urea Unfolded Rhodanese," *J. Biol. Chem.* 266:13587–13591.

Mendoza et al., (1991) "Intermediates in the Chaperonin–assisted Refolding of Rhodanese Are Trapped at Low Temperature and Show a Small Stoichiometry," *J. Biol. Chem.* 266:16973–16976.

Price et al., (1993) "The Unfolding and Attempted Refolding of the Bacterial Chaperone Protein GroEL (cpn60)," *Biochim. Biophys. Acta* 1161–52–58.

Pushkin et al., (1992) "High Molecular Weight Pea Leaf Protein Similar to The GroE Protein of Escherichia coli," *Biochim. Biophys. Acta* 704:379–384.

Schmidt et al., (1994) "Symmetric Complexes of GroE Chaperonins as Part of the Functional Cycle," *Science* 265:656–659.

Taguchi et al., (1991) "A Chaperonin from a Thermophilic Bacterium, Thermus Thermophilus, That Controls Refoldings of Several Thermophilic Enzymes," *J. Biol. Chem.* 266:22411–22418.

Taguchi et al., (1994) "Monomeric Chaperonin–60 and Its 50–kDa Fragment Possess the Ability to Interact with Non––native Proteins, to Suppress Aggregation, and to Promote Protein Folding," *J. Biol. Chem.* 269:8529–8534.

Todd et al., (1994) "Dynamics of the Chaperonin ATPase Cycle: Implications for Facilitated Protein Folding," *Science* 265:659–666.

Viitanen et al., (1992) "Mammalian Mitochondrial Chaperonin 60 Functions as a Single Toroidal Ring," *J. Biol. Chem.* 267:695–698.

Wiech et al., (1982) "Hsp90 Chaperones Protein Folding in Vitro," *Nature* 358:169–170.

Yoshida et al., (1993) "A Chaperonin From a Thermophilic Bacterium, Thermus Thermophilus," *Phil. Trans. R. Soc. Lond B339:305–312.*

Zeilstra–Ryalls et al., (1991) "The Universally Conserved GroE (Hsp60) Chaperonins," *Annu. Rev. Microbiol.* 45:301–325.

Zheng et al., (1993) "GroEL, GroES, and ATP–dependent Folding and Spontaneous Assembly of Ornithine Transcarbamylase," *J. Biol. Chem.* 268:7489–7493.

Fig. 1A  Fig. 1B

METHODS AND COMPOSITIONS FOR PROMOTING PROTEIN FOLDING

FIELD OF THE INVENTION

The present invention relates generally to the field of protein folding and, more particularly, to methods and compositions for promoting the folding of polypeptide chains in vitro.

BACKGROUND OF THE INVENTION

Improved methodologies for maximizing protein production through recombinant gene expression is an on-going effort in the art of particular interest is the development of methodologies for maximizing the folding of polypeptide chains produced by recombinant gene expression as a way of producing commercially useful quantities of functional proteins.

A variety of eukaryotic vectors and eukaryotic host cell systems have been developed for the production of proteins by recombinant gene expression. While eukaryotic cells, typically yeast's and mammalian cell lines, have been used in the production of a variety of mammalian proteins, a number of problems associated with such cells still exist. Specifically, high levels of protein production typically are not easily obtained in eukaryotic expression systems. In addition, eukaryotic host cells typically have stringent growth requirements and have slow growth rates in culture. Consequently, the production of large quantities of recombinant proteins requires more than simply culturing a host cell transfected with an expression vector. This is particularly true when the gene of interest encodes a protein that is poorly expressed, e.g., is not produced in abundance and/or is only transiently produced under natural, physiological conditions.

In contrast, prokaryotic host cell systems, typically bacterial host cell systems, have proven capable of generating large quantities of proteins by recombinant gene expression. Typically, bacterial host cells have much simpler growth requirements and grow significantly faster than eukaryotic cells thereby enabling the production of large quantities of recombinant proteins at a fraction of the cost of producing equivalent quantities of the same protein in a eukaryotic system. To date, the prokaryotic organism *Escherichia coli* (*E. coli*), typically has been the organism of choice. A variety of *E. coli* expression vectors, *E. coli* host strains and methods for expressing recombinant proteins in *E. coli* are well known, and thoroughly discussed in the art. See, for example, Rosenberg et al. (1983) *Methods in Enzymology* 101:123; Milman (1987) *Methods in Enzymology* 153:; Duffaud et al. (1987) *Methods in Enzymology* 153:; Sambrook et al. ed., (1989), *Molecular Cloning: A Laboratory Manual,* 2nd Edit., Cold Spring Harbor Laboratory Press; Ausubel et al., ed., (1989) *Current Protocols in Molecular Biology,* John Wiley & Sons, NY, the disclosures of which are incorporated herein by reference.

High levels of protein production by recombinant gene expression in *E. coli,* typically results in the formation of insoluble aggregates of the unfolded polypeptide in the *E. coli* cytoplasm. The insoluble aggregates, known as "inclusion bodies", may be purified by methodologies well known in the art, and described for example, in Sambrook et al., (1989) supra. Following expression of the protein of interest, inclusion bodies are isolated, washed, and the insoluble inclusion bodies solubilized in buffer. Useful solubilization agents include for example, chaotropic salt and detergents. A number of strategies useful in identifying effective solubilization agents are described in Glover (1987) *DNA Cloning: A Practical Approach,* IRL Press, Oxford, the disclosure of which is incorporated herein by reference.

The solubilized polypeptides subsequently are folded in vitro to form a biologically active protein. Folding is initiated by diluting the solubilization reagent, however, optimal folding conditions typically are found by empirical experimentation. Folding of proteins containing cysteine residues has proved difficult because incorrect intramolecular and intermolecular disulfide bonds may form during folding preventing the polypeptide from attaining its biologically active conformation. To date, only a few functional mammalian proteins, i.e., growth hormone and synthetic hemoglobin, have been produced following their expression *E. coli.* Accordingly, the development of procedures for folding polypeptides produced by recombinant gene expression in *E. coli* is an on-going effort in the art.

Although the mechanisms by which polypeptide chains fold into their native conformations are poorly understood, it is believed that folding of a polypeptide chain is initiated by the collapse of hydrophobic domains into the interior of the molecule, formation of stable secondary structures; and/or the formation of covalent interactions, i.e., disulfide bridges, which stabilize the polypeptide in a particular conformation. Subsequent folding appears to occur through a limited number of pathways involving distinct intermediates. These intermediates appear to be in rapid equilibrium with the denatured state and are only converted slowly to the native biologically active state (Gething et al., supra).

Although some polypeptides have the ability to assemble spontaneously into their native biologically active conformation in vitro many commercially useful proteins do not. There appear to be several competing processes which together influence whether a polypeptide chain will fold spontaneously and include, for example, the formation of unfavorable intramolecular and/or intermolecular interactions that together result in the aggregation of the polypeptide chains. It is believed that the aggregated polypeptide chains may no longer participate in a productive folding pathway.

It has been found, however, that a family of extrinsic helper proteins, called chaperonins, may prevent unfavorable interactions between unfolded polypeptide chains thereby assisting the polypeptides to fold along productive folding pathways. Chaperonins are oligomeric protein complexes that mediate the correct assembly of a preselected polypeptide chain, but which are not themselves components of the final functional protein. Chaperonins not only promote the folding of monomeric proteins but also oligomeric protein complexes. The roles of chaperonins in protein folding have been reviewed extensively. See, for example: Zeilstra-Ryalls et al. (1991) *Annu. Rev. Microbiol.* 45:301–325; Hartl et al. (1992) *Annu. Rev. Biophys. Biomol. Struct.* 21:293–322; Lorimer (1992) *Curr. Opin. Struct. Biol.* 2:26–34; Gething et al. (1992) *Nature* 322:33–45; and Ellis et al. (1991) *Annu. Rev. Biochem.* 60:321–347, the disclosures of which are incorporated herein by reference.

The term chaperonin originally was used to define a class of molecular chaperones homologous in structure to *E. coli* GroEL. The earliest evidence for the involvement of the chaperonins in post-translational events was the demonstration that *E. coli* groEL plays an integral role in phage head development (Sternberg et al. (1973) *J. Mol. Biol.* 76:25–44; Georgopoulos et al. (1973) *J. Mol. Biol.* 76:45–60). Members of this protein family, however, are present in all prokaryotes and in those organelles of eukaryotic cells, such as mitochondria (also known as heat shock protein-60) and chloroplasts (also known as ribulose-1,5-bisphosphate carboxylase subunit binding protein), that have probable endosymbiotic origin. These proteins, which have been renamed chaperonin-60 (cpn60), typically are large tetradecameric complexes composed of 14 identical non covalently associated subunits arranged as two stacked heptameric toroidal rings having intrinsic ATPase activity (Hohn et al. (1979) *J. Mol. Biol.* 129:359–373; Hendrix (1979) *J. Mol. Biol.* 129:375–392; Puskin et al. (1982) *Biochim. Biophys. Acta* 704:379–384; Ishii et al. (1992) *FEBS Let.* 299:169–174). It has been shown, however, that a functional mammalian mitochondrial cpn60 complex may exist as a single heptameric toroidal ring (Viitanen et al. (1992) *J. Biol. Chem.* 267:695–698).

Each subunit of the cpn60 complex has an apparent relative molecular weight of about 60 kD as determined by sodium dodecyl sulfate polyacrylamide gel electrophoresis (SDS-PAGE). The 60 kD monomeric subunits are referred to herein as monomeric subunits of cpn60 or cpn60m. Lissin et al. (1990) *Nature* 348:339–342 show that the in vitro assembly of oligomeric *E. coli* cpn60 complex from monomeric subunits of cpn60 requires $Mg^{2+}$ and ATP.

Furthermore, it has been found that in the presence of $Mg^{2+}$ and ATP the cpn60 complex may associate with a co-chaperonin called cpn10 to form holo-chaperonin. Native cpn10 is believed to exist as a oligomeric complex comprising seven identical subunits each of which have an apparent molecular weight of about 10 kD as determined by SDS-PAGE (Chandrasekhar et al. (1986) *J. Biol. Chem.* 261:1214–12419; Lubben et al. (1990) *Proc. Natl. Acad. Sci. USA* 87:7683–7687; Hartman et al. (1992) *Proc. Natl. Acad. Sci. USA* 89:3394). Like cpn60 complexes, the cpn10 complexes have been found in both prokaryotes and eukaryotes. For example, a prokaryotic cpn10 complex, called GroES, has been isolated from *E. coli* and a eukaryotic cpn10 homologue has been isolated from mitochondria.

Presently, the functional bacterial chaperonin complex or holo-chaperonin is believed to comprise the tetradecameric form of cpn60 and the heptameric form of cpn10. It is believed also that the binding of heptameric cpn10 to tetradecameric cpn60 regulates the ATPase activity of the cpn60 complex, and further, that cpn10 is required optimal activity of the cpn60 complex in protein folding (Chandrasekhar (1986), supra; Viitanen (1990) *Biochem.* 29:5665–5671; Martin et al. (1991) *Nature* 352:36–42).

Studies have shown that the amino acid sequences of the monomeric subunits of cpn60 and cpn10, are highly conserved between prokaryotes and eukaryotes (Hemmingsen et al. (1988) *Nature* 333:330–334; Zeilstra-Ryalls (1991), supra, Ellis et al. (1991), supra). For example, yeast mitochondrial chaperonin 60 protein shares 45% identical residues with wheat plastid chaperonin 60, and 54% identical residues with *E. coli* chaperonin 60 (Ellis et al. (1991), supra).

In vitro studies show that the tetradecameric form of chaperonin-60 typically binds unfolded polypeptide chains thereby arresting their folding. It is believed that heptameric cpn10 coordinates conformational changes of in the cpn60 complex thereby allowing the folding of the polypeptide chain to occur by a process of stepwise release (Martin et al., (1991) supra). Structural and biochemical studies have shown that the binding site for the unfolded polypeptide chain is in the central cavity of the tetradecameric cpn60 complex (Langer et al. (1992) *EMBO J.* 11:4757–4765; Braig et al. (1993) *Proc. Natl. Acad. Sci. USA.* 90:3978–3982).

Goloubinoff et al. (1989) *Nature* 324:884–889 show that the oligomeric chaperonin-60 complex is required for the generation of a functional holo-chaperonin complex. Heretofore, it was believed that only functional holo-chaperonin complexes comprising oligomeric chaperonin-60 and heptameric chaperonin-10 are capable of promoting the folding of polypeptide chains in vitro. Under certain experimental conditions, for example, in the presence of chaotropic agents it may be difficult to maintain the stability of functional holo-chaperonin complex. Accordingly, it is desirable to develop protein compositions which promote the folding of polypeptide chains in vitro irrespective of whether or not the proteins are functionally active as monomers or oligomers. In addition, it is desirable to develop simpler procedures for promoting the folding of polypeptide chains in vitro.

Accordingly, it is an object of the instant invention to provide a composition comprising monomeric subunits of cpn60, or truncated fragments thereof, which promote the folding of a preselected polypeptide chain in vitro. It is another object of the invention to provide immobilized monomeric subunits of cpn60, or fragments thereof, which promote the folding of a preselected polypeptide chain in vitro. It is another object of the invention to provide methods using the aforementioned compositions for folding preselected polypeptide chains in vitro. Importantly, it is another object of the instant invention to provide a means for producing commercially-feasible quantities of biologically active proteins following their expression in a heterologous, specifically a prokaryotic, expression system.

These and other objects and features of the invention will be apparent from the description, drawings, and claims which follow.

SUMMARY OF THE INVENTION

It has been discovered that monomeric subunits of chaperonin 60 are biologically active in promoting the folding of polypeptide chains in vitro. Accordingly, the monomeric subunits of chaperonin 60 may be used as a means for folding polypeptide chains which are unable to fold spontaneously into their biologically active conformations in vitro.

In its broadest aspect the invention provides a method for folding a preselected polypeptide chain in vitro. The method comprises the steps of: providing a sample of the polypeptide in an inactive conformation; mixing with the polypeptide an isolated monomeric subunit of chaperonin-60, or a truncated fragment thereof; and incubating the mixture under conditions and for a time sufficient for the monomeric subunit of chaperonin-60 to interact with and promote the folding of the preselected polypeptide chain from an inactive conformation into an active conformation thereby to form a functional polypeptide having biological activity.

As used herein, the term "preselected polypeptide chain" is understood to mean any polypeptide known to have biological activity when folded into its native conformation. For example, the preselected polypeptide may comprise an amino acid sequence which when folded into its active conformation functions as an enzyme, toxin, hormone, growth factor, cell differentiation factor, lymphokine, cytokine, regulatory protein, structural protein, receptor, binding site, or antimetabolite.

As used herein, the terms "chaperonin-60 or cpn60" are understood to mean any oligomeric protein complex that binds an unfolded polypeptide chain but in the absence of additional factors is incapable of promoting the folding of the polypeptide chain in vitro. The oligomeric complex comprises either seven or fourteen non covalently associated protein subunits each of which have an apparent relative molecular weight of about 60 kD as determined by SDS-PAGE. Chaperonin-60 requires $Mg^{2+}$, ATP and a co-chaperonin, namely a chaperonin-10, to form a functional complex that promotes the folding of the unfolded polypeptide chain into a biologically active conformation.

As used herein, the terms "monomeric subunit of cpn60 or cpn60m" are understood to mean one of the aforementioned 60 kD subunits which in the absence of $Mg^{2+}$, ATP or chaperonin 10 are capable of promoting the folding of a preselected polypeptide chain from an inactive to an active conformation.

As used herein, the term "truncated fragment of cpn60m" is understood to mean any portion of the monomeric subunit of cpn60 that has a domain operative to promote the folding of another polypeptide chain but which itself is substantially incapable of forming an oligomeric complex with another monomeric subunit of cpn60.

In another aspect, the invention provides a composition for promoting the folding of a preselected polypeptide chain into its biologically active conformation. Specifically the invention provides a composition comprising an isolated truncated fragment of the monomeric subunit of chaperonin-60. The truncated fragment is capable of promoting in vitro the folding of a preselected polypeptide chain from an inactive conformation into an active conformation thereby to form a folded polypeptide having biological activity.

In another aspect, the invention provides a composition comprising an isolated monomeric subunit of chaperonin-60, or a fragment thereof that is immobilized onto a solid surface. The immobilized monomeric subunit of chaperonin 60, or truncated fragment thereof, is active in promoting the folding of a preselected polypeptide chain from an inactive conformation to an active conformation thereby forming a folded polypeptide having predetermined biological activity. The monomeric subunit may be immobilized covalently onto the solid surface.

It is contemplated that the monomeric subunit of chaperonin-60, or the truncated fragment thereof, may be immobilized onto the surface of a particle or a bead. The resulting particles may be packed into a chromatographic column and a solution containing unfolded polypeptide of interest passed through the column. The eluate may be harvested and the sample reapplied to the column in order to enhance the fraction of the folded polypeptide in the sample. Folded, active protein subsequently may be isolated from the eluate. Alternatively, the folding reaction may be performed as a batch reaction by mixing immobilized monomeric subunits of chaperonin 60, or immobilized fragments thereof, with a buffer containing the polypeptide to be folded. At the end of the reaction the particles subsequently may be removed from the buffer, for example, by sedimentation or filtration, and the isolated particles subsequently reused in further folding reactions.

In another aspect, the invention provides monomeric subunits that are capable of promoting the folding of polypeptide chains in the absence of $Mg^{2+}$ and ATP.

In another aspect, the invention provides methods for isolating monomeric subunits of chaperonin-60 useful in the practice of the instant invention. Specifically, the invention provides methods for isolating monomeric subunits of chaperonin-60 from a prokaryotic organism. A preferred source is the thermophilic organism *Thermus thermophilus*. It is contemplated that the monomeric subunits of cpn60 isolated from *T. thermophilus* may be useful in promoting the folding of polypeptide chains in vitro at elevated temperatures. Alternatively, a gene encoding the monomeric subunit of *T. thermophilus* chaperonin-60 may be isolated, cloned into a suitable expression vector, and recombinant *T. thermophilus* chaperonin-60 produced in a heterologous expression system. The resulting protein subsequently may be isolated, folded if necessary, and used in the practice of the instant invention.

In a preferred aspect, the invention provides a truncated fragment corresponding to the C-terminal portion of chaperonin 60 and having an apparent molecular weight of about 50 kD as determined by SDS-PAGE. The N-terminal amino acid of the 50 kD fragment corresponds to an amino acid located at position 79 in the amino acid sequence of native monomeric chaperonin 60. Accordingly, the 50 kD fragment lacks the amino acid sequence corresponding to the first 78 amino acids at the N-terminus of an intact monomeric subunit of chaperonin 60.

The truncated fragments of monomeric chaperonin 60 may be produced either by the proteolytic digestion of purified monomeric subunits of chaperonin 60 or by recombinant DNA methodologies, for example, a truncated version of a gene encoding a fragment of chaperonin 60 may be expressed in, and subsequently isolated from a suitable host cell. The resulting truncated fragments of monomeric chaperonin 60 subsequently may be used in the practice of the instant invention In still another aspect, the invention provides methods and compositions useful in folding polypeptide chains produced by recombinant gene expression. For example, a gene encoding a polypeptide of interest may be isolated, ligated into an expression vector, transfected into, and expressed in a suitable host cell. Currently preferred host cells are prokaryotic, i.e., *E. coli*, host cells. During expression of the gene of interest in *E. coli*, the resulting polypeptide chains typically form insoluble aggregates in the *E. coli* cytoplasm. The resulting aggregates subsequently may be isolated, washed,, solubilized in a suitable buffer, and the solubilized polypeptides folded using the methods and compositions described herein.

DETAILED DESCRIPTION OF THE INVENTION

It has been discovered that isolated monomeric subunits of chaperonin-60 (cpn60m), or truncated fragments thereof, may interact with, and promote the folding of an unfolded polypeptide chain from an inactive into a biologically active conformation in vitro. Accordingly, methods have been developed using isolated monomeric subunits of chaperonin-60, or truncated fragments thereof, for folding polypeptide chains lacking the propensity to fold spontaneously in vitro.

The instant method font promoting the folding of a preselected polypeptide chain in vitro comprises the steps of: providing a sample of the polypeptide to be folded; mixing the polypeptide with an isolated monomeric subunit of chaperonin-60, or a truncated fragment thereof; and incubating the mixture under conditions and for a time sufficient for the monomeric subunit of chaperonin-60, or the truncated fragment thereof, to interact with .and promote the folding of the preselected polypeptide chain from an inactive conformation into an active conformation.

The use of monomeric subunits of chaperonin-60 in folding reactions has several advantages over using the intact holo-chaperonin complexes. For example, the monomeric subunits may be used under experimental conditions that favor the dissociation of the holo-chaperonin complexes. If the conditions are such that the holo-chaperonin complex dissociates to form, for example, tetradecameric cpn60 and heptameric cpn10, then the unfolded polypeptide chain may actually bind the tetradecameric complex. Studies have shown, however, that the unfolded polypeptide while bound to the tetradecameric complex is prevented from folding into an active conformation. In addition, monomeric subunits of chaperonin-60 are active in buffers less complex than those used for intact holo-chaperonin thereby simplifying the reaction conditions. For example, in vitro folding studies show that the order in which $Mg^{2+}$, ATP and heptameric cpn10 are added to tetradecameric cpn60 significantly affects the efficiency of the folding reaction (Martin et al. (1991) supra), however, monomeric subunits of chaperonin-60 still promote the folding of polypeptide chains in the absence of cofactors such as ATP, $Mg^{2+}$, and heptameric cpn10.

It is contemplated that the compositions disclosed herein may be useful in folding polypeptide chains produced by recombinant gene expression methodologies. For example, the polypeptide chain of interest may function an enzyme, toxin, hormone, growth factor, cell differentiation factor, lymphokine, cytokine, regulatory protein, structural protein, receptor, binding site, or an anti-metabolite when folded into its native, biologically active conformation.

Methods for obtaining monomeric subunits of chaperonin-60, as well as other material aspects concerning the nature and utility of these monomeric subunits, including how to make and how to use the subject matter claimed, will be further understood from the following, which constitutes the best mode currently contemplated for practicing the invention.

I. Preparation of Monomeric Subunits of Chaperonin 60

Monomeric subunits of chaperonin 60 may be prepared by a variety of approaches. In one approach the monomers may be purified directly from a natural source, i.e., from an organism or organelle containing holo-chaperonin. During this approach, either holo-chaperonin complexes or chaperonin-60 complexes may be purified and the monomeric subunits of chaperonin-60 subsequently isolated from the aforementioned complexes. Alternatively., monomers of chaperonin-60 may be produced by recombinant gene expression technologies well known in the art.

A. Purification From Natural Sources

Purification of monomeric subunits chaperonin-60 from natural sources currently is the preferred approach for isolating monomers useful in the practice of the invention. In this approach, monomeric subunits subsequently are isolated from either purified holo-chaperonin or oligomeric chaperonin-60 complexes.

When isolated holo-chaperonin complexes are used as a starting material, the complexes preferably are denatured to produce a mixture of denatured monomeric subunits of chaperonin-60 and chaperonin-10. The resulting denatured monomers of chaperonin 60 and chaperonin-10 subsequently are separated, for example, by high pressure liquid chromatography, harvested and refolded prior to use. Methods for isolating native holo-chaperonin complexes are discussed elsewhere. For example, methods for isolating holo-chaperonin complexes from the thermophilic organism *T. thermophilus* are described in: Ishii et al. (1992) *FEBS Let.* 299:169–174; and Taguchi et al. (1991) *J. Biol. Chem.* 266:22411–22418, the disclosures of which are incorporated herein by reference.

Briefly, *T. thermophilus* cells are harvested, suspended in a lysis buffer comprising 25 mM Tris-HCl, pH 7.5, 5 mM $MgCl_2$, 100 mM dithiothreitol, and sonicated for 5 min. at 4° C. The crude extract then is processed by harvesting the supernatant following centrifugation, diluting the extract in lysis buffer to give a final protein concentration of 10 mg/ml, and by precipitating the complexes with ammonium sulfate (30–60% saturation). The precipitate then is harvested, dissolved in and dialyzed against lysis buffer. The resulting solution then is applied to a DE52-cellulose column equilibrated in the same buffer. The column then is washed with lysis buffer containing 50 mM NaCl and the complexes eluted with lysis buffer containing 100, 250, and then 400 mM NaCl. Fractions eluted at 250 mM NaCl then are pooled, concentrated, applied to a Sepharose CL6B column equilibrated with lysis buffer containing 100 mM $Na_2SO_4$. Fractions that elute with the void volume are pooled and stored at 4° C. as suspensions in 60% ammonium sulfate until further use.

Methods for isolating monomeric subunits of chaperonin-60 and chaperonin-10 complexes from *T. thermophilus* holo-chaperonin are described in Taguchi et al. (1994) *J. Biol. Chem.* 269:8529–8534, the disclosure of which is incorporated herein by reference.

Briefly, the *T. thermophilus* holo-chaperonin complex is denatured in organic solvent, for example trifluoroacetic acid (TFA) to produce denatured monomeric subunits of Th-cpn60 and Th-cpn10. The resulting polypeptide chains, then are separated, for example, by reverse phase high pressure liquid chromatography using a linear gradient of acetonitrile, and the eluted fractions containing Th-cpn60m and Th-cpn 10 collected. The isolated, but unfolded polypeptides then are dried in vacuo and solubilized in a buffer comprising a denaturant, for example, guanidine hydrochloride. The unfolded proteins subsequently are allowed to refold by the diluting the concentration of the denaturant in the buffer.

When isolated chaperonin-60 complexes are used as a starting material, the complexes subsequently may be disaggregated to generate the monomeric subunits of chaperonin 60. Methods useful in the isolation of chaperonin-60 complexes have been discussed previously are so are not described in detail herein. See for example, Hohn et al. (1979) *J. Mol. Biol.* 129:359–373; Hendrix (1979) *J. Mol. Biol.* 129:375–392; and Chandrasekar (1986) *J. Biol. Chem.*

261:12414–12419, the disclosures of which are incorporated herein by reference.

The isolated chaperonin-60 complexes subsequently may be denatured in organic solvent, i.e., TFA, the resulting unfolded monomeric subunits purified, for example, by chromatography, and refolded using the methodologies described hereinabove. The resulting monomeric subunits of chaperonin-60 may be used to the mediate the folding of other polypeptide chains using the methods described below.

B. Preparation of Monomeric Chaperonin-60 By Recombinant Gene Expression

It is contemplated that recombinant monomers useful in the practice of the instant invention may be prepared using standard recombinant DNA methodology and/or automated chemical nucleic acid synthesis methodology well described in the art and as disclosed hereinbelow.

Accordingly, the construction of DNAs encoding biosynthetic monomeric subunits of chaperonin 60 may be performed using known techniques involving the use of various restriction enzymes which make sequence specific cuts in DNA to produce blunt ends or cohesive ends, DNA ligases, techniques enabling enzymatic addition of sticky ends to blunt-ended DNA, construction of synthetic DNAs by assembly of short or medium length oligonucleotides, cDNA synthesis techniques, and synthetic probes for isolating genes of members of the chaperonin family. Various promoter sequences and other regulatory DNA sequences used in achieving expression, and various types of host cells are also known and available. Conventional transfection techniques, and equally conventional techniques for cloning and subcloning DNA are useful in the practice of this invention and known to those skilled in the art. Various types of vectors may be used such as plasmids and viruses including animal viruses and bacteriophages. The vectors may exploit various marker genes which impart to a successfully transfected cell a detectable phenotypic property that can be used to identify which of a family of clones has successfully incorporated the recombinant DNA of the vector.

One method for obtaining DNA encoding the monomeric subunits of chaperonin-60 disclosed herein is by assembly of synthetic oligonucleotides produced in a conventional, automated, polynucleotide synthesizer followed by ligation with appropriate ligases. For example, overlapping, complementary DNA fragments comprising 15 bases may be synthesized semi manually using phosphoramidite chemistry, with end segments left unphosphorylated to prevent polymerization during ligation. One end of the synthetic DNA is left with a "sticky end" corresponding to the site of action of a particular restriction endonuclease, and the other end is left with an end corresponding to the site of action of another restriction endonuclease. Alternatively, this approach can be fully automated. The DNA encoding the biosynthetic constructs may be created by synthesizing longer single strand fragments (e.g., 50–100 nucleotides long) and then ligating the fragments. In alternative approaches a gene encoding a monomeric subunit of chaperonin-60 may be isolated by colony hybridization and/or by polymerase chain reaction amplification protocols well known in the art.

The DNA constructs then may be integrated into an expression vector and transfected into an appropriate host cell for protein expression. Useful host cells include E. coli, Saccharomyces, the insect/baculovirus cell system, myeloma cells, and various other mammalian cells. In E. coli and other microbial hosts, the synthetic genes can be expressed as fusion proteins. Expression in eukaryotes can be accomplished by the transfection of DNA sequences encoding the biosynthetic protein of interest into myeloma or other type of cell line.

The vector additionally may include various sequences to promote correct expression of the recombinant protein, including transcriptional promoter and termination sequences, enhancer sequences, preferred ribosome binding site sequences, preferred mRNA leader sequences, preferred protein processing sequences, preferred signal sequences for protein secretion, and the like. The DNA sequence encoding the gene of interest also may be manipulated to remove potentially inhibiting sequences or to minimize unwanted secondary structure formation. The recombinant monomeric chaperonin-60 protein also may be expressed as a fusion protein. After being translated, the protein may be purified from the cells themselves or recovered from the culture medium.

For example, if the gene is to be expressed in E. coli, it may first be cloned into an expression vector. This is accomplished by positioning the engineered gene downstream of a promoter sequence such as Trp or Tac, and a gene coding for a leader peptide such as fragment B of protein A (FB). The resulting fusion proteins accumulate in refractile bodies in the cytoplasm of the cells, and may be harvested after disruption of the cells by French press or sonication. The refractile bodies may be solubilized, and the expressed proteins isolated and folded using the methods described in Section IA, hereinabove.

II. Preparation of Truncated Fragments of Monomeric Chaperonin-60

Truncated fragments of monomeric chaperonin-60 may be used in the practice of the instant invention. Preferred fragments of chaperonin-60 comprise a domain operative to promote the folding of other polypeptide chains but which are substantially incapable of forming oligomeric complexes with other monomeric subunits of chaperonin 60. Studies have shown that amino acids located at the N-terminus of monomeric chaperonin-60 stabilize the resulting tetradecameric complex (Horovitz et al. (1993) J. Biol. Chem. 268:9957–9959; Horovitz et al. (1993) J. Mol. Biol. 231:58–64). Accordingly, removal of these amino acids either by site directed replacement or by deletion of amino acid sequences containing these residues may reduce, or even prevent complex formation.

Truncated fragments of monomeric chaperonin 60 may be prepared by a variety of methodologies, for example, by proteolytic digestion of isolated monomers of chaperonin-60 or by recombinant DNA methodologies.

A preferred procedure :for producing truncated fragments of chaperonin 60 involves proteolytically digesting isolated monomeric subunits of chaperonin 60, and isolating the resulting fragments. It is contemplated that any commercially available proteolytic enzyme, for example, trypsin, chymotrypsin, papain, pepsin, proteinase K, pronase, lysylendopeptidase, carboxypeptidase, aminopeptidase, or a combination thereof, may be used to produce fragments useful in the practice of the instant invention. Furthermore, it is contemplated that immobilized proteolytic enzymes may be useful in producing proteolytic fragments of chaperonin-60.

Briefly, the isolated monomeric subunits of chaperonin-60 are mixed with the proteolytic enzyme and incubated under standard reaction conditions well known in the art. Following digestion, the resulting fragments subsequently may be fractionated, for example, by size exclusion chromatography, and the activity of the purified fragments in promoting protein folding assayed using the procedures described below. It is appreciated the judicious choice of specific enzymes, reaction conditions, and purification protocols is within the skill of the art.

Using the recombinant DNA methodologies, a recombinant gene encoding a truncated fragment chaperonin-60 may be prepared, for example, by digesting a gene encoding the intact subunit of chaperonin-60 with sequence specific restriction endonucleases and/or exonucleases, or by deleting sequences by site directed mutagenesis methodologies. The resulting sequences subsequently may be ligated into an appropriate expression vector, transfected into, and then expressed in an appropriate host cell. The recombinant truncated fragment of chaperonin-60 subsequently may be isolated, and folded, if necessary, using the methods described above.

III. Immobilization of the Monomeric Subunits of Chaperonin-60

It is contemplated that the monomeric subunits of chaperonin-60, including truncated fragments thereof may be immobilized onto solid surfaces in order simplify folding of preselected polypeptide chains on a commercial scale. The monomeric subunits of chaperonin-60 or truncated fragments thereof prepared in accordance with the instant invention may be immobilized on a solid surface such that they interact with, and promote the folding of a preselected polypeptide chain.

Currently, the preferred solid surfaces are the surfaces of particulate beads or resins, i.e., resins that have been developed for use in chromatographic matrices. It is appreciated, however, that the choice of particular types of resins will be dependent upon a number of factors, i.e., molecular weight of the polypeptide to be folded, stability of the particles under particular folding conditions; chemical reactivity of the active moieties on the surface of the resin; and chemical reactivity of the monomeric subunit of chaperonin 60 to be immobilized on the resin.

Currently preferred resins include, but are not limited to: TSK gel AF-Tresol Toyopearl (Tosoh); EAH Sepharose (Pharmacia); cyanogen bromide activated Sepharose (Pharmacia); activated CH Sepharose (Pharmacia); epoxy-activated Sepharose (Pharmacia); Thiopropyl Sepharose (Pharmacia); activated-Thiol Sepharose (Pharmacia); and Affigel (Biogel). Methodologies for immobilizing the monomeric subunits of chaperonin-60, or the truncated fragments thereof, onto the resin of choice preferably are performed in accordance with the manufacturers instructions.

Resins derivatized witch either monomeric subunits of chaperonin-60, or truncated fragments thereof, then may be packed into a chromatographic column. Accordingly, a reaction buffer containing the unfolded polypeptide of interest subsequently may be passed through the column and the resulting folded, biologically active polypeptide isolated from the eluate. It is contemplated that the eluate may be passed through the column several times in order to increase the fraction of the folded polypeptide in sample prior to purification.

Alternatively, the folding reaction may be performed as a batch reaction by simply adding immobilized monomeric subunits of chaperonin-60, or truncated fragments thereof, to a buffer containing the unfolded polypeptide chain of interest. Following incubation under appropriate conditions the resulting biologically active protein may be purified from the reaction mixture. In addition, the particles may be isolated from the reaction mixture, e.g., by sedimentation or filtration, and reused in other folding reactions.

IV. Preparation of the Polypeptide to be Folded

As mentioned hereinabove, the instant invention has particular utility in the commercial production of proteins which have been synthesized by recombinant DNA methodologies and which lack the ability to fold spontaneously into an active conformation following synthesis.

The preselected recombinant polypeptides preferably are prepared using the same methodologies as those discussed in section IB, hereinabove. It is contemplated that any standard expression system, for example, *E. coli*, Saccharomyces, mammalian cell lines, baculovirus/insect cell system may be used to generate the recombinant polypeptides of interest. Preferred vectors, host cells, and culture conditions are within the skill of the art and so art not discussed in detail herein.

The instant invention, however, has particular utility in folding polypeptides synthesized at high levels by recombinant gene expression in *E. coli*. During high levels of expression in *E. coli*, the unfolded polypeptide chains typically aggregate and form insoluble inclusion bodies. The inclusion bodies subsequently may be isolated, washed, and solubilized using procedures within the level of skill in the art. The solubilized but unfolded polypeptide chains may be folded using the methods and compositions described below.

V. Folding Conditions

The polypeptide to be folded preferably is provided in a buffer comprising a solubilization agent, for example, a chaotropic salt or detergent. Folding subsequently is initiated by diluting the solubilization agent with a buffer containing monomeric subunits of chaperonin-60, or truncated fragments thereof. The monomeric subunits of chaperonin-60, or the truncated fragments thereof may be immobilized on the surface of a solid particle.

Currently preferred reaction buffers include phosphate buffers, and more specifically include potassium phosphate buffers. The preferred pH range for performing the folding reaction is from about pH 6 to about pH 8. The preferred stoichiometry of the unfolded polypeptide chain to the monomeric subunits of chaperonin 60, or truncated fragments, in the reaction mixture typically is from about 1:1 to about 1:10 on a molar basis. Preferred temperatures for performing the folding reactions typically are in the range from about 20° C. to about 80° C. Preferred incubation times typically are from about 30 minutes to about 2 hours. It is appreciated, however, that the optimal folding conditions for a particular polypeptide chain of interest may be found by varying the aforementioned conditions by routine experimentation.

Following folding, the resulting biologically active protein may be purified from the reaction mixture by standard procedures, i.e., immunoaffinity and/or chromatographic protocols, within the level of skill in the art.

The present invention will be explained by the following examples. However the scope of the present invention is not restricted by these examples.

Example 1

Preparation of *T. thermophilus* Holo-chaperonin

The holo-chaperonin complex comprising tetradecameric cpn60 and heptameric cpn10 was isolated from *T. thermo*-

*philus* by the procedure described in Taguchi et al. (1991) supra.

*T. thermophilus* strain HBS (ATCC 27634) was cultured at 75° C. under strong aeration in a medium containing 10 g of yeast extract, 10 g of polypeptone, and 2 g of NaCl/liter. Cells were harvested at the late log phase and stored at −20° C. until use. The frozen cells were thawed, :suspended in a 2-fold volume of Buffer A (25 mM Tris-HCl, pH 7.5, 5 mM $MgCl_2$, 100 mM dithiothreitol), and sonicated for 5 min at 4° C. The supernatant (crude extract) was diluted with Buffer A to give a final protein concentration of 10 mg/ml, and fractionated by ammonium sulfate precipitation (30–60% saturation). The precipitate was dissolved in, and dialyzed against Buffer A.. The resulting solution then was applied to a DE52-cellulose column equilibrated with Buffer A. The column was washed with Buffer A containing 50 mM NaCl and the complexes subsequently eluted with Buffer A containing 100, 250, and then 400 mM NaCl. Fractions eluted at 250 mM NaCl were pooled and concentrated by ultrafiltration (Amicon, ultrafiltration cell 8200). The concentrated solution was applied onto a Sepharose CL6B column equilibrated with Buffer A containing 100 mM $Na_2SO_4$. Fractions eluted in the void volume were pooled and stored at 4° C. as a suspension in 60% ammonium sulfate until further use.

Example 2

Preparation of Monomeric Subunits of *T. thermophilus* Chaperonin-60 and Oligomeric Chaperonin-10

Monomeric subunits of *T. thermophilus* cpn60 (Th-cpn 60m) and heptameric *T. thermophilus* cpn10 complexes (Th-cpn10) were isolated using methodologies described previously (Taguchi et al. (1994), supra).

Briefly, the *T. thermophilus* holo-chaperonin complex, prepared in Example 1, was denatured in 0.1% trifluoroacetic acid thereby to form denatured monomeric subunits of Th-cpn60 and Th-cpn10. The resulting polypeptide chains, then were separated by reverse phase high pressure liquid chromatography. Specifically, the sample was applied to a Sensyu Pak C4 Hi-pore column, the column developed with a linear gradient of acetonitrile, and the eluted fractions containing Th-cpn60m and Th-cpn10 collected.

The samples of purified monomeric Th-cpn60 and Th-cpn 10 were dried in vacuo and solubilized in a buffer containing 6M guanidine hydrochloride. The denatured proteins subsequently were allowed to refold at 60° C. by the diluting the buffer 40.-fold with 50 mM Tris-HCl, pH 7.5. The refolded Th-cpn60 proteins did not reassemble into oligomer complexes and existed in solution as monomers (Th-cpn60m). In contrast, under the same conditions, the refolded monomeric subunits of Th-cpn10 Reassembled into oligomeric complexes, probably heptameric complexes.

Example 3

Preparation of Truncated Fragments of Monomeric Subunits of *T. thermophilus* Chaperonin-60

A 50 kD tryptic fragment of the Th-cpn60m was prepared by digesting Th-cpn60m, isolated and refolded in Example 2, with the proteolytic enzyme trypsin.

Briefly, 2.8 units of immobilized L-1-tosoylamindo-2-phenylethyl chloromethyl ketone-trypsin (Pierce) was mixed with 15 mg of purified Th-cpn60m in 3 ml of buffer comprising 50 mM Tris HCl, pH 7.5 and the resulting mixture incubated for 3 hours at 25° C. Fractionation of the reaction mixture by SDS-PAGE revealed that under the experimental conditions used, a significant portion of Th-cpn60m in the sample had been digested to form a truncated tryptic fragment having a relative molecular weight of about 50 kD.

The truncated 50 kD fragment subsequently was purified by size exclusion chromatography using a G3000SWxl column (Tosoh). Briefly, the proteolytic reaction mixture was added to, and eluted from the column in a buffer comprising 25 mM Tris-HCl pH 7.0, and 100 mM sodium sulfite.

The amino terminal sequence of the truncated 50 kD fragment subsequently was determined by standard N-terminal amino acid sequencing procedures. The N-terminal amino acid was found to correspond to the amino acid sequence starting at Threonine 79 of the 60 kD intact monomeric subunit of Th-cpn60.

Example 4

Figure 1A:
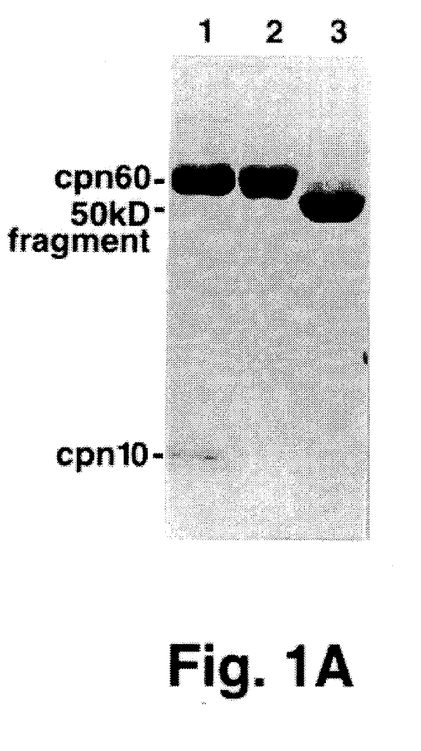
FIGS. 1A and 1B shows the electrophoretic separation patterns of *T. thermophilus* holo-chaperonin (holo-cpn); isolated monomers of *T. thermophilus* cpn60 (Th-cpn60m); and a 50 kD tryptic fragment of *T. thermophilus* Th-cpn 60m. The samples were fractionated by either denaturing (gel A) or non-denaturing (gel B) polyacrylamide gel electrophoresis in the presence or absence of SDS, respectively. In both gels, lane 1 contains holo-cpn, lane 2 contains isolated Th-cpn60m, and lane 3 contains the isolated 50 kD tryptic fragment of Th-cpn60m. After fractionation, the proteins were visualized with Coomassie Brilliant blue. The concentrations of polyacrylamide in gels A and B were 15% and 7.5%, respectively.
Figure 1B:
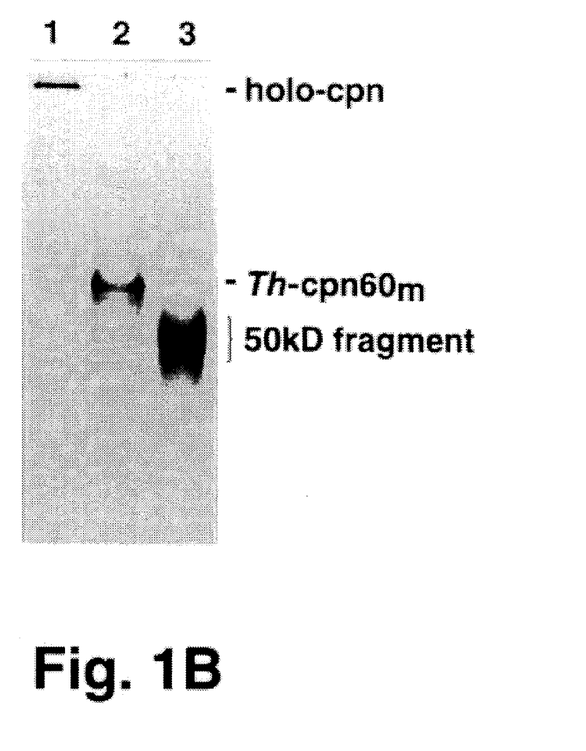

Characterization of *T. thermophilus* Holo-chaperonin, Monomeric Subunits of Chaperonin-60 and the 50 kD Truncated Fragment The purified samples of *T. thermophilus* holo-chaperonin, Th-cpn60m, and the 50 kD fragment, prepared in examples 1, 2, and 3, subsequently were characterized by denaturing and non-denaturing PAGE and the results are shown in FIG. 1A and FIG. 1B, respectively.

The denaturing gel was run in the presence of SDS whereas the non-denaturing, or native gel, was run in the absence of SDS. In both gels, lane 1 contains holo-cpn, lane 2 contains Th-cpn60m, and lane 3 contains the 50 kD tryptic fragment of Th-cpn60m. Following fractionation under standard conditions, the proteins were visualized with the stain Coomassie Brilliant Blue.

Denaturing SDS-PAGE (FIG. 1A) shows that the isolated *T. thermophilus* holo-cpn complex comprises subunits of Th-cpn60 and Th-cpn10 (lane 1). In contrast, the isolated monomeric subunits of Th-cpn60 (lane 2) and the 50 kD tryptic fragment (lane 3) are free of Th-cpn10.

Non denaturing PAGE (FIG. 1B) shows that *T. thermophilus* holo-cpn complex exists as a high molecular weight oligomeric complex (lane 1). In contrast, the purified fractions of Th-cpn60m (lane 2) and the 50 kD fragment (lane 3) exist primarily in their monomeric states.

The Th-cpn60m and the truncated 50 kD fragment were also characterized by size exclusion chromatography. Briefly, the samples were ,applied to a Tosoh G3000SWxl column in a buffer comprising 25 mM Tris HCl pH 7.0, and 100 mM sodium sulfate .and the column developed with the same buffer. Analysis of the elution profiles confirms that both the Th-cpn60m and the 50 kD truncated fragment exist as monomers in solution.

When $Mg^{2+}$ and ATP were added to Th-cpn60m in the absence of heptameric Th-cpn10, less that 10% of the Th-cpn60m subunits oligomerized to form a tetradecameric complex. The 50 kD fragment did not oligomerize even in the presence of $Mg^{2+}$, ATP and heptameric Th-cpn10. Only very low levels of ATPase activity, less than. 5% of intact *T. thermophilus* holo-chaperonin ATPase activity, were detected in the preparations of the Th-cpn60m and the 50 kD fragment.

Example 5

Immobilization of Th-cpn60m and Bovine Serum Albumin (BSA) On Solid Particles Samples of Th-cpn60m, prepared in Example 2, and BSA, purchased from Sigma Chemical Co., were immobilized onto the surface of AF-tresol Toyopearl:650 M particles (Tosoh) in accordance with the manufacturers instructions.

Briefly, 6 mg of the particles dispersed in 0.1M phosphate buffer pH 7.5, 0.5 M NaCl were mixed with 20 µg of either Th-cpn60m or BSA, and the resulting mixtures incubated overnight at 4° C. Following incubation, the particles were washed with 0.5M NaCl and any unreacted groups on the surface of the particles inactivated by incubating the particles for one hour in buffer comprising 0.1M Tris-HCl pH 8.0 and 0.5M NaCl. The resins were used directly in the folding reactions described below.

Example 6

Folding of Rhodanese In Vitro

Bovine mitochondrial rhodanese, purchased from Sigma Chemical Co., was used as an exemplary protein in the folding experiments disclosed herein because denatured rhodanese is substantially incapable of folding spontaneously back into its biologically active conformation in vitro. Furthermore, rhodanese routinely is used as a model protein by artisans in the field of protein folding.

Rhodanese was denatured for at least 30 min at room temperature in a buffer containing 50 mM potassium phosphate pH 7.8, 5 mM dithiothreitol, and 6M guanidine hydrochloride. The denatured sample was diluted 25-fold with a buffer containing 50 mM potassium phosphate pH 7.8, 50 mM sodium thiosulfonate, 5 mM dithiothreitol and one of the following additives, namely: 3.3 µM of Th-cpn60m as prepared in example 2; a mixture of 2.5 µM Th-cpn60m and 2.5 µM Th-cpn10 complex; a mixture of 2.5 µM Th-cpn60m and 2.5 µM Th-cpn 10 in the presence of 1 mM $Mg^{2+}$ and 1 mM ATP; 3.9 µM of the truncated 50 kD fragment of Th-cpn60m; immobilized Th-cpn60m prepared by the method described in Example 5; or immobilized bovine serum albumin (immobilized BSA). No additive was added to the control buffer. After dilution, the final concentration of rhodanese in the buffer was 0.13 µM.

The samples subsequently were mixed and incubated for 60 minutes at 37° C. After 60 minutes, the rhodanese activity in each sample was determined using the method described in Sorbo et al. (1953) *Acta Chem. Scand.* 7:1129–1136, the disclosure of which is incorporated herein by reference. The results are summarized in Table 1 below and are presented as percentages of the rhodanese activity prior to denaturation.

TABLE 1

| Dilution buffer Additive | Rhodanese Activity (%) |
|---|---|
| Control | 4.5 |
| Th-cpn60m | 24.7 |
| Th-cpn60m & Th-cpn10 | 24.6 |
| Th-cpn60m & Th-cpn10 & Mg-ATP | 25.2 |
| 50 kD fragment | 35.0 |
| immobilized BSA | 0.0 |
| immobilized Th-cpn60m | 10.0 |

Table 1 shows that both Th-cpn60m and its 50 kD fragment are effective at promoting the folding of denatured rhodanese in vitro. In addition, immobilized Th-cpn60m is capable of promoting the folding of denatured polypeptide chains in vitro. Furthermore, both Th-cpn60m and the 50 kD fragment promote the folding of polypeptide chain even in the absence of $Mg^{2+}$, ATP, and/or chaperonin-10.

The invention may be embodied in other specific forms without departing from the spirit or essential characteristics thereof. The present embodiments therefore are considered in all respects as illustrative and non restrictive, the scope of the invention being indicated by the appended claims rather than by the foregoing description, and all changes which come within the meaning and range of equivalency of the claims are therefore intended to be embraced therein.

What is claimed is:

1. A method for promoting folding of a preselected polypeptide chain into its biologically active conformation, said method comprising the steps of:
   (a) providing said preselected polypeptide chain in an inactive conformation,
   (b) admixing said preselected polypeptide chain with an isolated monomeric subunit of chaperonin-60, or a truncated fragment thereof, to form a mixture, wherein said monomeric subunit of chaperonin60, or said truncated fragment thereof, is characterized as being operative to promote, in vitro, the folding of said polypeptide chain from an inactive conformation to its active conformation, and
   (c) incubating said mixture under conditions and for a time sufficient for said monomeric subunit of chaperonin-60, or said truncated fragment thereof, to promote, in vitro, the folding of said polypeptide chain from said inactive conformation into its biologically active conformation, thereby to form a polypeptide having biological activity.

2. The method of claim 1, wherein said truncated fragment comprises a proteolytic fragment of monomeric chaperonin-60 having a molecular weight of about 50 kD as determined by SDS-PAGE and an N-terminal amino acid that corresponds to an amino acid located at position 79 in monomeric chaperonin-60.

3. The method of claim 1, wherein said monomeric subunit of chaperonin-60, or said truncated fragment thereof, promotes the folding of said polypeptide in the absence of $Mg^{2+}$ and ATP.

4. The method of claim 1, comprising the additional step of isolating said monomeric subunit of chaperonin-60, or said truncated fragment thereof, from a prokaryotic organism.

5. The method of claim 4, wherein said prokaryotic organism is *Thermus thermophilus*.

6. The method of claim 1, comprising the additional step of immobilizing said monomeric subunit of chaperonin-60, or said truncated fragment thereof, onto a solid surface prior to admixing said monomeric subunit of chaperonin-60, or said truncated fragment thereof, with said polypeptide.

7. The method of claim 6, wherein said solid surface is the surface of a particle.

8. The method of claim 1, comprising the additional step of admixing, in step (b), isolated chaperonin-10 with said polypeptide and said monomeric subunit of chaperonin-60, or said truncated fragment thereof.

9. The method of claim 1, comprising the additional step of isolating said polypeptide from a prokaryotic host cell.

10. A composition for promoting folding of a preselected polypeptide chain into its biologically active conformation, said composition comprising:

an isolated truncated fragment of monomeric chaperonin-60, wherein said truncated fragment of monomeric chaperonin-60 is characterized in that upon mixture with said polypeptide chain in an inactive conformation said truncated fragment is operative to promote, in vitro, the folding of said polypeptide chain from an inactive conformation to its biologically active conformation, thereby to form a folded polypeptide chain having biological activity.

11. A composition for promoting folding of a preselected polypeptide chain into its biologically active conformation, said composition comprising:

an isolated monomeric subunit of chaperonin-60, or a truncated fragment thereof, immobilized onto a solid surface, wherein said monomeric subunit of chaperonin-60, or said truncated fragment thereof when immobilized onto said solid surface, is characterized in that upon mixture with said polypeptide chain in an inactive conformation is operative to promote, in vitro, the folding of said polypeptide chain from an inactive conformation into its biologically active conformation thereby to form a folded polypeptide having biological activity.

12. The composition of claim 11, wherein said solid surface is the surface of a particle.

13. The composition of claim 10 or 11, wherein said truncated fragment comprises a proteolytic fragment of monomeric chaperonin-60 having a molecular weight of about 50 kD as determined by SDS-PAGE and an N-terminal amino acid that corresponds to an amino acid located at position 79 in monomeric chaperonin-60.

14. The composition of claim 10 or 11, wherein said monomeric subunit of chaperonin-60, or said truncated fragment thereof, promotes the folding of said polypeptide in the absence of $Mg^{2+}$ and ATP.

15. The composition of claim 10, or 11 wherein said monomeric subunit of chaperonin-60, or said truncated fragment thereof, is isolated from a prokaryotic organism.

16. The composition of claim 15, wherein said prokaryotic organism is *Thermus thermophilus*.

17. The composition of claim 10 or 11, further comprising isolated chaperonin-10.

18. The composition of claim 10 or 11, wherein said preselected polypeptide chain is a polypeptide chain produced in a prokaryotic host cell.

\* \* \* \* \*